United States Patent [19]

Kerby et al.

[11] Patent Number: 4,997,963
[45] Date of Patent: Mar. 5, 1991

[54] ORGANO-METALLIC COMPLEX OF MOLYBDENUM CARBOXYLATE AND ETHYLENE DIAMINE

[75] Inventors: Michael C. Kerby, Annandale; Bryan W. Eichhorn, Madison, both of N.J.

[73] Assignee: Exxon Research and Engineering Company, Florham Park, N.J.

[21] Appl. No.: 468,492

[22] Filed: Jan. 23, 1990

Related U.S. Application Data

[62] Division of Ser. No. 288,513, Dec. 22, 1988, Pat. No. 4,916,222.

[51] Int. Cl.$^5$ ............................................. C07F 11/00
[52] U.S. Cl. ...................................................... 556/63
[58] Field of Search ........................................... 556/63

[56] References Cited

PUBLICATIONS

Cotton, *Chem. Soc. Rev.*, 4, 27–53 (1975).
Cotton et al., *Advanced Inorganic Chemistry*, N.Y., John Wiley & Sons, 1980.

*Primary Examiner*—Arthur C. Prescott
*Attorney, Agent, or Firm*—Jay Simon

[57] ABSTRACT

A novel organo metallic complex useful as a metathesis catalyst and having the formula $$[Mo_2(O_2CR)_2(H_2NCH_2CH_2NH_2)_4]$$
$$[(O_2CR)_2] \cdot H_2NCH_2CH_2NH_2$$

is formed by reacting a carboxylate such as dimolybdenum tetra acetate with ethylene diamine and crystallizing the complex.

3 Claims, 1 Drawing Sheet

ORGANO-METALLIC COMPLEX OF MOLYBDENUM CARBOXYLATE AND ETHYLENE DIAMINE

CROSS REFERENCE TO RELATED APPLICATIONS

This application is a Rule 1.60 Divisional of U.S. Ser. No. 288,513, filed Dec. 22, 1988 now U.S. Pat. No. 4,916,222.

FIELD OF THE INVENTION

This invention relates to a new organo-metallic complex having a highly unsaturated metal-metal bond. More particularly, this invention relates to a new material useful as a metathesis catalyst, formed by reacting a molybdenum carboxylate complex preferably the acetate with ethylene diamine (EN) to form a complex wherein two bridging EN's replace two acetate groups which are, in turn, hydrogen-bonded to the hydrogens of the bridging EN's.

BACKGROUND OF THE INVENTION

The insolubility of dimolybdenum tetra acetate in water or organic solvents makes its highly unsaturated metal-metal bond virtually useless in promoting chemical reactions with organic substrates. The chemistry of a related compound, dimolybdenum trifluoro-tetraacetate, which is soluble in organic solvents has been studied in relation to the highly unsaturated metal-metal bond.

The newly formed organo-metallic complex of this invention is useful in metathesis reactions, as well as for the oligomerization of alkenes or alkynes. An example of the metathesis reaction known in the literature is the reaction of the unsaturated molybdenum-molybdenum triple bond with an alkyne

The more unsaturated molybdenum-molybdenum quadruple bond produced by this invention will produce more advantageous reactions

One object of this invention is to provide a new, more reactive material for carrying out metathesis related, coupling, and oligomerization reactions.

SUMMARY OF THE INVENTION

A new organo-metallic complex having the formula $$[Mo^2 (O^2CR)_2 (H^2NCH_2CH_2NH_2)_4][(O_2CR)_2]^{500}$$
$$H_2NCH_2CH_2NH_2$$

wherein R may be $C_1$-$C_5$, preferably methyl, is formed by treating the molybdenum carboxylate complex, preferably the acetate, neat, with a bidentate ligand such as ethylene diamine (EN), heating the mixture to dissolve the complex, and cooling the resulting solution to crystallize the organo-metallic complex.

DETAILED DESCRIPTION OF THE INVENTION

Figure 1:
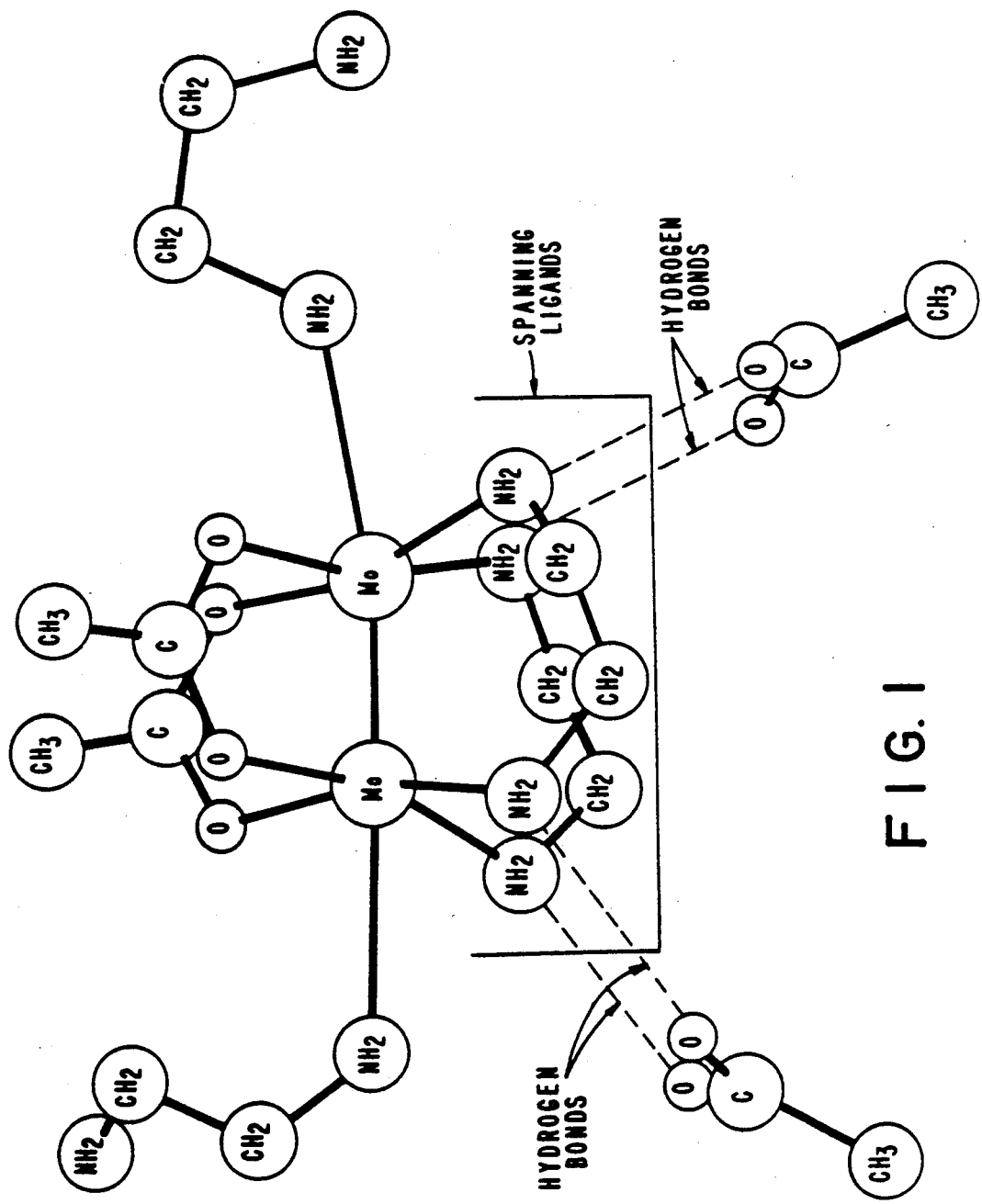
FIG. 1 is representative of a three dimensional arrangement of the new complex illustrated with the dimolybdenum tetra acetate. The displaced carboxylate groups are hydrogen bonded to the hydrogens attached to the nitrogen atoms of EN.

The reacting materials are readily available, and the reaction occurs when a large excess of the ligand, used neat, is added to the molybdenum carboxylate complex and the resulting mixture is heated for a period of time sufficient to dissolve completely the complex in the ligand, usually about 10 minutes to an hour. The mixture may be heated to about 40° C. to about 60° C. or higher but usually below the decomposition temperature of the ligand.

Reaction pressure is not critical and atmospheric pressure is quite advantageous. The reaction occurs in the substantial absence of water, e.g., in a dry box under argon or other inert gas. The resulting solution is then cooled, e.g., by simply removing the heating source, and the organo-metallic complex crystallizes during cooling, e.g., to room temperature or to about 30° C. Excess ligand can be removed by decanting, filtration, or similar means leaving the crystalline organo-metallic complex.

The metathesis process is important commercially in the polymerization of cycloalkenes and in the SHOP process (Shell Higher Olefins Process), as illustrated in *The Organo-Metallic Chemistry of the Transition Metals*, Robert H. Crabtree, published by John Wiley & Sons, New York, N.Y., 1988, pps. 264-267, 272-275.

Illustrative of the reactions that can be effected with the organo-metallic complex are the following:

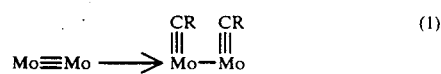

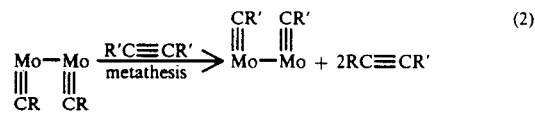

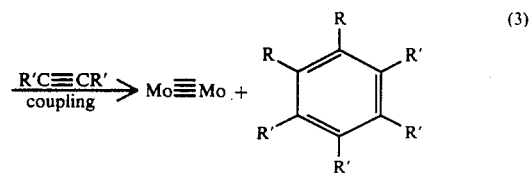

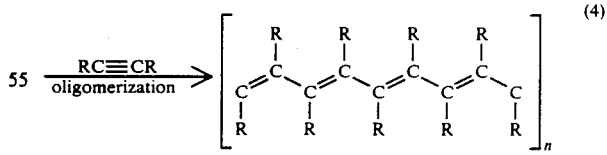

Each of these reactions are effected with an excess of alkyne (R'C≡CR', or RC≡CR), in polar solvents such as lower alcohols, e.g., methanol, ethanol, or water, at moderate reaction temperatures, e.g., 50° to 100° C., and atmospheric pressure.

R may be alkyl (i.e. $C_1$-$C_{10}$ preferably $C_1$-$C_5$) or aryl
and
R' may be alkyl (i.e. $C_1$-$C_{10}$ preferably $C_1$-$C_5$) or aryl

EXAMPLES

This invention can be illustrated by the following examples.

EXAMPLE 1

Preparation of the dimolybdenum tetra acetate ethylene diamine complex (a) To a vial in a dry box under argon was added $Mo_2(O_2CCH_3)_4$ (103 mg, 0.241 mmol) and dry ethylenediamine (en) (2 mL). The resulting orange-red solution was warmed to 50° C. for 10 minutes and allowed to cool to 30° C. After 12 hours air-sensitive orange-red crystals of the complex (155 mg, 80% yield) were collected by filtration and dried in vacuo.

(b) Using identical conditions as in (a) with $Mo_2(O_2CCH_3)_4$ (100 mg, 0.234 mmol) and ethylenediamine (2 mL) collected the complex (140 mg, 72% yield).

$^1$H NMR ($D_2O$) δ 2.57 (s, 20 H), 1.7 (s, 12 H); $^{13}$C NMR (en) δ 184 (br s), 181 (br s), 177 (s), 25.3 (s), 24.2 (br s), 21.8 (br s); IR (cm$^{-1}$, KI) 1670, 1578, 1530, 1420, 1340; MS (EI): 428 (M+- 5 en), 369 (M+- 5 en, $O_2CCH_3$); TGA: loss of 1 en (70° C.), 4 en (90°-120° C.), $Mo_2(O_2CCMe)_4$ (255° C.).

Analysis calculated for $Mo_2(O_2CCH_3)_4$ $(H_2NCH_2CH_2NH_2)_5$: C, 29.68; H, 7.20; N, 19.23; Mo, 26.34. Found: C, 28.68; H, 6.83; N, 19.13; Mo, 26.57.

Molecular structure of the complex: Selected bond distances (Å): Mo-Mo 2.124 (1), Mo-O 2.115 (4), Mo-N 2.230 (6), Mo-N 2.69 (1), O-C 1.268 (9), N-C 1.45 (1), NH . . . O 2.85 (1). Selected bond angles (°): O-Mo-Mo 91.1 (1), O-Mo-O 87.1 (2), O-Mo-N 92.2 (3), Mo-Mo-N 170.3 (4).

EXAMPLE 2

Use Organo-Metallic complex to form an Adduct with Phenyl acetylene.

(a) To a vial in a dry box under argon was added $Mo_2(O_2CCH_3)_4$ (118 mg, 0.276 mmol) and dry ethylenediamine (en) (2 mL). To the resulting orange-red solution was added phenylacetylene (73 mg, 0.715 mmol, 2.6 eq). After 5 days air-sensitive purple crystals of the adduct were collected by filtration and dried in vacuo (108 mg, 52% yield). Spectroscopic evidence points to two compounds in solution, A and B.

(b) Under identical conditions as in (a) with $Mo_2(O_2CCH_3)_4$ (96 mg, 0.224 mmol), ethylenediamine (2 mL), PhC≡CH (27 mg, 0.26 mmol, 1.2 eq) collected adduct (74 mg, 42% yield).

$^1$H NMR ($D_2O$ 8.63 (s, 1 H), 7.53 (t, J=7.6 Hz, 2 $H_m$), 7.33 (t, J=7.3 Hz, 1 $H_p$), 7.24 (d, J=7.6 Hz, 2 $H_o$) A; 7.62 (s, 1 H), 7.45 (t, J=7.6 Hz, 2 $H_m$), 7.33 (t, J=7.3 Hz, 1 $H_p$), 7.12 (d, J=7.6 Hz, 2 $H_o$) B; 3.39 (m, a), 3.25 (m, b) 3.18 (m, c), 3.13 (m, d), 2.90 (s, e), 2.89 (s, f), 1.92 (s, 12 H) with a-f=20 H; $^{13}$C NMR ($CD_3OD$) 180.26 (s), 147.3 (s), 145.8 (s), 144.3 (s), 134.9 (s), 131.9 (s), 130.8 (s), 130.6 (s), 130.4 (s), 130.2 (s), 130.11 (s), 130.0 (s), 129.4 (s), 128.0 (s), 127.5 (s), 126.6 (s), 126.2 (s), 66.0 (s), 56.6 (s), 56.4 (s), 46.30 (s), 46.11 (s), 45.63 (s), 45.06 (s), 44.84 (s), 44.74 (s), 44.31 (s), 43.79 (s), 43.10 (s), 42.71 (s), 42.56 (s), 42.03 (s), 41.81 (s), 25.75 (s), 24.52 (s); IR (cm$^{-1}$, KI) 3225, 3120, 2940, 2890, 1690, 1576, 1558, 1507, 1452, 1398, 1335, 1291, 1228, 1132, 1050, 1015, 952, 918, 880, 830, 770, 710, 645, 550, 460; TGA: loss of 4 en (142° C.), 1 en+$C_6H_6$ (221° C.), 21% (4162 C.), 9% (555° C.), 24% remains (>800° C.).

Analysis calculated for $Mo_2(O_2CCH_3)_4$ $(H_2NCH_2CH_2NH_2)_5$ $(C_6H_5CCH)$: C, 37.59; H, 7.04; N, 16.86. Found: C, 37.61; H, 7.51; N, 16.75.

What is claimed is:

1. A process for preparing a molybdenum containing organo-metallic complex which comprises dissolving a molybdenum compound of the formula $Mo_2(O_2CR)_4$ with ethylene diamine, neat and wherein R is $C_1$-$C_5$ alkyl.

2. The process of claim 1 wherein R is methyl.

3. The process of claim 1 wherein the mixture of the molybdenum compound and ethylene dimaine is heated and the complex is formed by crystallization.

* * * * *